United States Patent
Watanabe et al.

(10) Patent No.: US 7,235,170 B2
(45) Date of Patent: *Jun. 26, 2007

(54) BIOSENSOR

(75) Inventors: Motokazu Watanabe, Toyonaka (JP); Takahiro Nakaminami, Kyoto (JP); Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 597 days.

This patent is subject to a terminal disclaimer.

(21) Appl. No.: 10/344,671

(22) PCT Filed: May 13, 2002

(86) PCT No.: PCT/JP02/04624

§ 371 (c)(1),
(2), (4) Date: Feb. 14, 2003

(87) PCT Pub. No.: WO02/093151

PCT Pub. Date: Nov. 21, 2002

(65) Prior Publication Data

US 2003/0175841 A1 Sep. 18, 2003

(30) Foreign Application Priority Data

May 15, 2001 (JP) ............... 2001-144382

(51) Int. Cl.
*C12Q 1/26* (2006.01)
(52) U.S. Cl. ............... 205/777.5; 204/403.01; 204/403.06; 204/403.1; 204/403.13; 435/14
(58) Field of Classification Search ............ 205/777.5; 204/403.01, 403.06, 403.1, 403.13; 435/14
See application file for complete search history.

(56) References Cited

U.S. PATENT DOCUMENTS

| | | | |
|---|---|---|---|
| 4,755,467 A | | 7/1988 | Scopes et al. |
| 5,064,618 A | * | 11/1991 | Baker et al. ............ 422/82.01 |
| 5,082,786 A | * | 1/1992 | Nakamoto ................ 257/253 |
| 5,120,420 A | * | 6/1992 | Nankai et al. ......... 204/403.11 |
| 5,177,012 A | | 1/1993 | Kim et al. |
| 5,543,024 A | * | 8/1996 | Hanazato et al. .......... 257/253 |
| 5,777,372 A | * | 7/1998 | Kobashi .................... 257/414 |
| 6,740,215 B1 | * | 5/2004 | Nakaminami et al. . 204/403.14 |

FOREIGN PATENT DOCUMENTS

EP   0 992 589 A2   4/2000

(Continued)

OTHER PUBLICATIONS

"Biosensor" ed., Shuichi Suzuki, Kodansha pp. 100-103, year not available.

*Primary Examiner*—Nam Nguyen
*Assistant Examiner*—Anthony Fick
(74) *Attorney, Agent, or Firm*—McDermott Will & Emery LLP (57) ABSTRACT

A biosensor that is highly responsive and capable of rapid and highly sensitive quantification of a specific component contained in a sample is provided. The biosensor of this invention comprises: an electrically insulating base plate; an electrode system comprising a working electrode and a counter electrode disposed on the base plate; and a reagent system comprising an oxidoreductase which catalyzes the oxidation reaction of glucose, gluconolactonase and a buffer. The buffer is selected from the group consisting of phthalic acid and its salts, maleic acid and its salts, succinic acid and its salts, phospholic acid and its salts, acetic acid and its salts, boric acid and its salts, citric acid and its salts, glycine, tris(hydroxymethyl)aminomethane, piperazine-N,N'-bis(2-ethane sulfonic acid) and the like.

11 Claims, 4 Drawing Sheets

FOREIGN PATENT DOCUMENTS

| | | |
|---|---|---|
| JP | 57-120853 A | 7/1982 |
| JP | 63-214662 | 9/1988 |
| JP | 64-68650 A | 3/1989 |
| JP | 1-107145 | 4/1989 |
| JP | 1-140054 | 6/1989 |
| JP | 3-202764 | 9/1991 |
| JP | 6-138080 A | 5/1994 |
| WO | WO 01/36955 | 11/2000 |

* cited by examiner

BIOSENSOR

TECHNICAL FIELD

The present invention relates to a biosensor for rapid and simple quantification of a specific component contained in a sample.

BACKGROUND ART

With the aim of realizing simple quantification of body fluid components by ordinary people, various types of biosensors have recently been developed which utilize the specific catalytic action of enzymes.

The following will describe a method of glucose quantification as one example of the method of quantifying a component contained in a sample solution. As an electrochemical method of glucose quantification, a method using the combination of glucose oxidase and an oxygen electrode or a hydrogen peroxide electrode is generally well-known (see "Biosensor" ed. by Shuichi Suzuki, Kodansha, for example).

Glucose oxidase selectively oxidizes glucose as a substrate to gluconolactone using oxygen as an electron mediator. In the process of the oxidation reaction of glucose by glucose oxidase in the presence of oxygen, oxygen is reduced to hydrogen peroxide. The decreased amount of oxygen is measured by the oxygen electrode, or the increased amount of hydrogen peroxide is measured by the hydrogen peroxide electrode. Since the decreased amount of oxygen and the increased amount of hydrogen peroxide are proportional to the content of glucose in the sample solution, glucose quantification is possible based on the decreased amount of oxygen or the increased amount of hydrogen peroxide.

As speculated from the reaction process, the above method has a drawback in that the measurement is affected by the oxygen concentration of the sample solution, and if the oxygen is absent in the sample solution, the measurement is infeasible.

Under such circumstances, glucose sensors have been developed which use, as the electron mediator, an organic compound or a metal complex such as potassium ferricyanide, a ferrocene derivative or a quinone derivative without using oxygen as the electron mediator. In the sensors of this type, the reduced form of the electron mediator which results from the enzyme reaction is oxidized on an electrode, and based on the amount of this oxidation current, the concentration of glucose contained in the sample solution can be determined. With the use of such an organic compound or metal complex as the electron mediator in place of oxygen, it is possible to form a reagent layer in which the electron mediator is carried with glucose oxidase on the electrode in a precise amount and in a stable state. Further, it is also possible to integrate the reagent layer, in an almost dry state, with the electrode system, and hence disposable glucose sensors based on this technique have recently been receiving a lot of attention. A typical example thereof is a biosensor disclosed in Japanese Patent Publication No. 2517153. With such a disposable glucose sensor, by simply introducing a sample solution into the sensor connected detachably to a measurement device, glucose concentration can be measured readily by the measurement device.

According to the measurement method using the above-described glucose sensor, the concentration of glucose in a sample can be determined in about 30 seconds based on the response current which is in the order of 1 to 10 $\mu A/cm^2$.

However, in recent years, it is anxiously desired in various fields to develop sensors capable of quantifying glucose more rapidly and with higher sensitivity.

Also, in conventional electrochemical glucose sensors, by the addition of a hydrophilic polymer such as carboxymethyl cellulose to the reagent layer, the measurement is prevented from being affected by vibrations given to the measurement device from outside. The hydrophilic polymer has another merit that it functions as a binder to immobilize the enzyme on the electrode moderately. The presence of the hydrophilic polymer, however, may cause changes in catalytic activity of glucose oxidase or thermodynamics of the hydrolytic reaction from gluconolactone to gluconic acid, thereby to cause accumulation of gluconolactone, which is a product of the oxidation reaction of glucose. The accumulation of gluconolactone causes the reverse reaction to proceed and causes the rate of the oxidation reaction of glucose to decrease. As a result, the amount of the reduced form electron mediator generated in a short reaction time is reduced, thereby resulting in a decrease in the magnitude of the response current to glucose, i.e., the sensitivity of the sensor. Particularly, in order to obtain a sufficient sensitivity to high concentrations of glucose, it becomes necessary to increase the reaction time for generating large amounts of the reduced form electron mediator, so that the measurement tends to require longer time.

In view of the above conventional problems, an object of the present invention is to provide a biosensor that is highly responsive and capable of rapid and highly sensitive quantification of a specific component in a sample.

DISCLOSURE OF INVENTION

A biosensor in accordance with the present invention comprises: an electrically insulating base plate; an electrode system comprising a working electrode and a counter electrode disposed on the base plate; and a reagent system comprising an oxidoreductase which catalyzes a reaction of oxidizing glucose to gluconolactone, gluconolactonase and a buffer, wherein the buffer is selected from the group consisting of phthalic acid and its salts, maleic acid and its salts, succinic acid and its salts, phospholic acid and its salts, acetic acid and its salts, boric acid and its salts, citric acid and its salts, glycine, tris(hydroxymethyl)aminomethane, piperazine-N,N'-bis(2-ethane sulfonic acid), N-(2-acetamide)iminodiacetic acid, N,N-bis(2-hydroxyethyl)-2-aminoethane sulfonic acid, 2-morpholinoethanesulfonic acid, imidazole, dimethyl glutaric acid, triethanolamine hydrochloride, collidine, N-tris(hydroxymethyl)methylglycine, and bis(2-hydroxyethyl)iminotris(hydroxymethyl)methane.

BEST MODE FOR CARRYING OUT THE INVENTION

A biosensor in accordance with the present invention comprises: an electrically insulating base plate; an electrode system comprising a working electrode and a counter electrode disposed on the base plate; and a reagent system comprising an oxidoreductase which catalyzes a reaction of oxidizing glucose to gluconolactone, gluconolactonase and a specific buffer.

Therein, the above-mentioned buffer is preferably selected from the group consisting of phthalic acid, phthalates, maleic acid, maleates, succinic acid, succinates, phospholic acid, phosphates, acetic acid, acetates, boric acid, borates, citric acid, citrates, glycine, tris(hydroxymethyl) aminomethane, and piperazine-N,N'-bis(2-ethane sulfonic acid).

In another embodiment of the present invention, the buffer is selected from the group consisting of N-(2-acetamide) iminodiacetic acid, N,N-bis(2-hydroxyethyl)-2-aminoethane sulfonic acid, 2-morpholinoethanesulfonic acid, imidazole, dimethyl glutaric acid, triethanolamine hydrochloride, collidine, N-tris(hydroxymethyl)methylglycine, and bis(2-hydroxyethyl)iminotris(hydroxymethyl) methane.

According to the present invention, gluconolactone, which is a product of the oxidation of glucose by the action of the oxidoreductase, is converted to gluconic acid by gluconolactonase. This facilitates the oxidation reaction of glucose, so that sufficient response can be obtained even when the measuring time is short. Also, by adjusting the pH of the reaction system, the activity of the oxidoreductase or gluconolactonase contained in the biosensor can be improved, so that the response characteristics of the sensor is further improved. Of the above-listed buffers, phthalic acid, phthalates, maleic acid, maleates, succinic acid, succinates and tris(hydroxymethyl)aminomethane are preferable since they have sufficiently high dissolution.

Therein, it is preferable that reagent system further comprise an electron mediator. Although the oxygen dissolved in the sample solution may be utilized as the electron mediator, it is preferable that the reagent system comprise an electron mediator. Examples of the electron mediator include metal complexes such as potassium ferricyanide, osmium-tris (bipyridinium) or ferrocene derivatives, quinone derivatives such as p-benzoquinone, phenazinium derivatives such as phenazine methosulfate, phenothiazinium derivatives such as methylene blue, nicotinamide adenine dinucleotide and nicotinamide adenine dinucleotide phosphoric acid. These electron mediators are used singly or in combination of two or more.

It is preferable that the reagent system further comprise a hydrophilic polymer. Examples of preferable hydrophilic polymers are carboxyethyl cellulose, hydroxyethyl cellulose, hydroxypropylcellulose, methyl cellulose, ethyl cellulose, ethyl hydroxyethyl cellulose, carboxymethyl ethyl cellulose, polyvinyl pyrrolidone, polyvinyl alcohol, polyamino acid such as polylysine, polystyrene sulfonic acid, gelatin and its derivatives, a polymer of acrylic acid or its salts, a polymer of methacrylic acid or its salts, starch and its derivatives, a polymer of maleic anhydride or its salts, and agarose gel and its derivatives. When the reagent system comprises such a hydrophilic polymer, the measurement is not affected by vibrations given to the measurement device from outside. The hydrophilic polymer also has a merit that it functions as a binder to immobilize the enzymes on the electrodes moderately.

The oxidoreductase which catalyzes the oxidation reaction of glucose, gluconolactonase and the buffer may be carried by the sensor while being mixed with each other. In this case, the manufacturing process of the biosensor becomes simple, and easy production of the reagent layer is possible. Further, since the oxidoreductase is present in the vicinity of gluconolactonase, gluconolactone produced by the action of the oxidoreductase is more promptly converted to gluconic acid by gluconolactonase. Therefore, the oxidation reactivity of glucose is improved, so that sufficient response can be obtained even when the measuring time is shorter.

The oxidoreductase which catalyzes the oxidation reaction of glucose and gluconolactonase may be carried by the sensor while being separated from each other. In this case, a buffer adequate for each enzyme can be mixed with each enzyme, or can be added to the vicinity of each enzyme, so that the activity of each enzyme can be improved more efficiently.

The gluconolactonase is preferably originated from one selected from the group consisting of *Escherichia coli*, yeast, man, rat, swine, bovine, *Aspergillus niger, Azotobacter vinelandii, Pseudomonas fluorescens, Zymomonas mobilis, Streptomyces coelicolor, Deinococcus radiodurans* and *Xylella fastidiosa*. Among them, one derived from *Escherichia coli*, yeast or *Aspergillus niger* is more preferable because of high productivity and sufficient activity.

The amount of the buffer carried by the sensor is preferably 5 nmol/mm$^2$ or less. In this case, the pH of the sample solution to be measured can be adjusted such that each enzyme can exhibit sufficient activity without impairing dissolution of gluconolactonase and the oxidoreductase which catalyzes the oxidation reaction of glucose.

Further, when such amount is carried, the response value to 0 mg/dl of glucose, i.e., blank response value, is not heightened, and a highly reliable biosensor can therefore be obtained. The amount of the buffer carried is more preferably 0.1 to 3 nmol/mm$^2$. For disposable sensors designed to measure 0.04 to 20 µl of blood as a sample solution, the amount is preferably in a range of 5 to 1000 nmol per sensor from the viewpoint of effectively smoothing the layer containing the buffer and of reducing the blank value.

The inclusion of the buffer in the reagent layer serves to smooth the reagent layer formed by application and drying of a solution. When a reagent layer is formed by drying an aqueous solution dissolving a reagent, the resultant reagent layer becomes rough or uneven because the reagent crystallizes out into coarse crystals, or for other reasons. This is evident especially when potassium ferricyanide is contained as the electron mediator. When the reagent layer contains the buffer, however, the resultant layer becomes smooth without such unevenness. This is probably because the crystals produced by drying a solution dissolving the buffer are more minute.

When the reagent layer is dissolved in a sample solution upon supply of the sample solution to the sensor, if the reagent layer has unevenness on its surface, air may come in between the sample solution and the unevenness of the reagent layer, possibly evolving air bubbles in the sample solution in which the reagent layer is dissolved. The evolution of the air bubbles hinders the sample solution from moving smoothly in the sample solution supply pathway, making the quantification difficult. Therefore, by smoothing the reagent layer, the above-described problem can be resolved. Further, the smooth reagent layer enables reduction in the volume or height of the sample solution supply pathway, realizing reduction in the amount of the sample solution.

The buffer preferably has a buffering capacity in a range of pH 4 to 8. With the use of such a buffer, when a sample solution is supplied and the reagent contained in the biosensor is dissolved in the sample solution, the solution constituting an enzyme reaction system is adjusted to around pH 4 to 8. In this pH range, the reactivity of the whole reaction system is improved, so that sufficient response can be obtained even when the measuring time is shorter.

The oxidoreductase which catalyzes the oxidation reaction of glucose is preferably selected from the group consisting of glucose oxidase, PQQ dependent glucose dehydrogenase, NAD dependent glucose dehydrogenase and pyranose oxidase. When glucose oxidase is used as the oxidoreductase which catalyzes the oxidation reaction of glucose, it is more preferable to use a buffer having a buffering capacity in a range of pH 4 to 6. When PQQ dependent glucose dehydrogenase, NAD dependent glucose dehydrogenase or pyranose oxidase is used as the oxidoreductase which catalyzes the oxidation reaction of glucose, it is more preferable to use a buffer having a buffering capacity in a range of pH 5 to 8.

The biosensor in accordance with the present invention may further comprise a cover member that is disposed on the base plate to form a sample solution supply pathway to the electrode system between the cover member and the base plate. This structure has an advantage that the amount of the sample can be regulated to a constant level. Also, in the case of using a buffer having a low dissolution, this structure allows the buffer to be carried on the cover member side separately from the enzyme. Further, in the case of carrying, on the biosensor, an amphipathic compound which will be described later, by carrying the amphipathic compound on the cover member side separately from the enzymes, the following advantage can be obtained. That is, an amphipathic compound layer is generally formed by a method of applying an organic solvent solution of an amphipathic compound and drying it. If the amphipathic compound layer is formed on a layer containing an enzyme, the organic solvent dissolving the amphipathic compound may exert an influence on the enzyme. Such influence of the organic solvent on the enzyme can be avoided by forming the amphipathic compound layer on the cover member side separately from the enzyme-containing layer.

The biosensor in accordance with the present invention may further comprise the amphipathic compound in the reagent system. As the amphipathic compound, lecithin, Triton X-100 and the like are particularly preferable. When the reagent system contains the amphipathic compound, due to the amphipathic action of the amphipathic compound, the sample solution supply pathway of the sensor becomes hydrophilic, so that a sample solution such as blood is promptly supplied into the sample solution supply pathway and the evolution of the air bubbles in the sample solution supply pathway can be prevented.

Examples of the sample which can be used in the biosensor of the present invention include blood, plasma, serum, glucose aqueous solution, culture fluid and fermented liquid.

In the following, the present invention will be described in terms of examples, but the present invention is not to be limited only to these examples.

EXAMPLE 1

Figure 1:
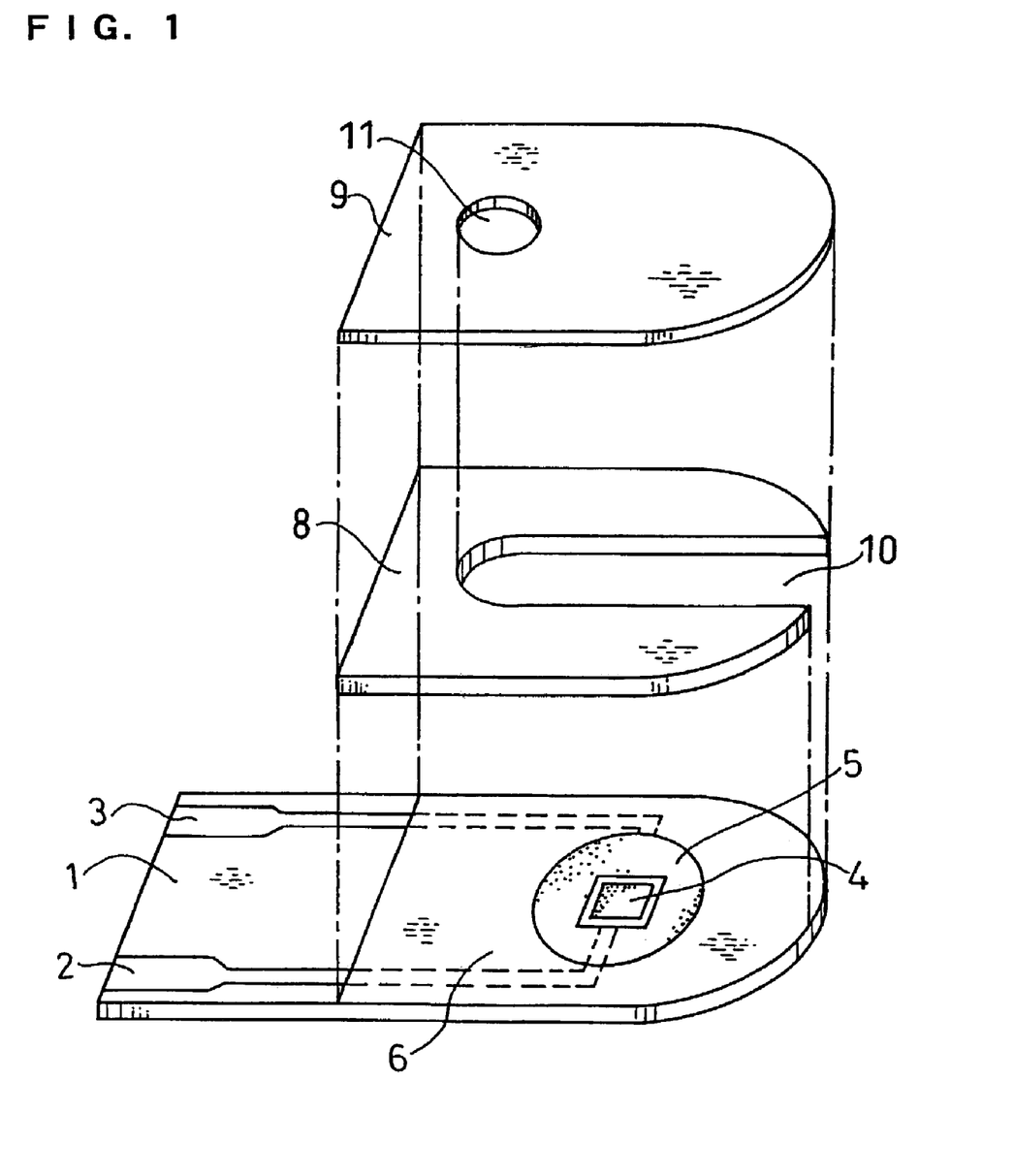
FIG. 1 is a perspective view of a biosensor from which the reagent system is omitted in one example of the present invention.

FIG. 1 is a decomposed perspective view of a glucose sensor from which the reagent system is omitted in this example. A silver paste was printed on an electrically insulating base plate 1 made of polyethylene terephthalate by screen printing to form leads 2 and 3. Subsequently, a conductive carbon paste containing a resin binder was printed on the base plate 1 to form a working electrode 4. This working electrode 4 is in contact with the lead 2. Further, an insulating paste was printed on the base plate 1 to form an insulating layer 6. The insulating layer 6 covers the outer peripheral portion of the working electrode 4, thereby to keep the area of exposed portion of the working electrode 4 constant. Then, a conductive carbon paste containing a resin binder was printed on the base plate 1 so as to be in contact with the lead 3, whereby a ring-like counter electrode 5 was formed.

After a reagent system was formed on the base plate 1 in a manner as described later, a mid cover 8 having a slit 10 and a top cover 9 having an air vent 11 were bonded thereto in a positional relationship as shown by the dash-dotted lines in FIG. 1, to fabricate a biosensor. A sample solution supply pathway is formed in the portion of the slit 10 of the mid cover 8 by combining the cover member consisting of the mid cover 8 and the top cover 9 with the base plate 1. The open end of the slit 10, which is at the end of the sensor, serves as a sample supply inlet to the sample solution supply pathway.

Figure 2:
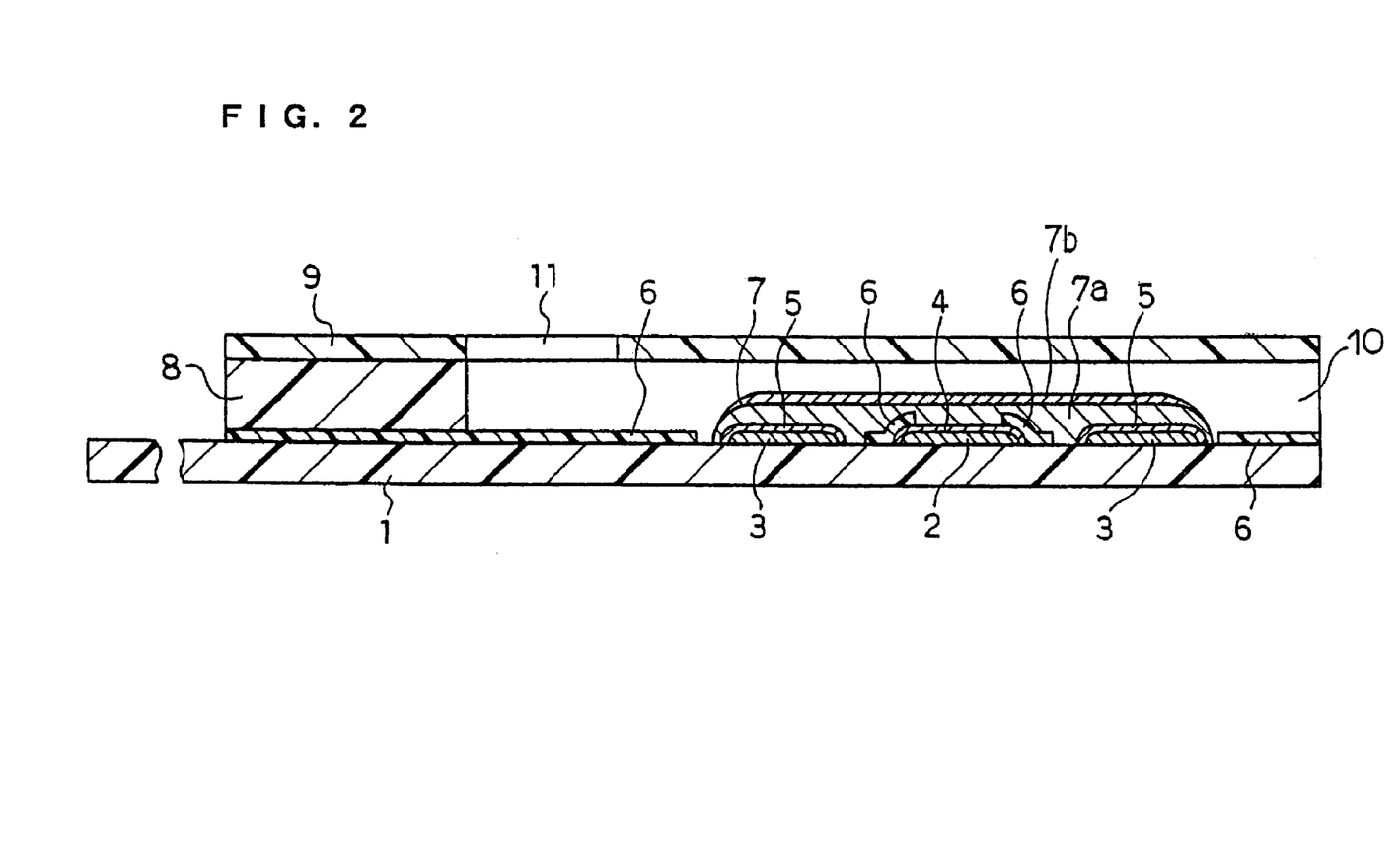
FIG. 2 is a longitudinal sectional view of the main part of the same biosensor.

FIG. 2 is a longitudinal sectional view of the biosensor of this example. First, on the base plate 1 on which the electrode system composed of the working electrode 4 and the counter electrode 5 was formed, a CMC layer 7a was formed by dropping a 0.5 wt % aqueous solution of carboxymethyl cellulose (hereinafter referred to as CMC), which is a hydrophilic polymer, in an amount of 5 µl and drying it. Next, glucose oxidase, which is an oxidoreductase that catalyzes the oxidation reaction of glucose, potassium ferricyanide, which is an electron mediator, and gluconolactonase originated from *Aspergillus niger* were dissolved in a 1 mM maleic acid buffer solution (pH6), which is a buffer. 4 µl of the solution was dropped on the CMC layer 7a and was dried to form a reagent layer 7b. Therein, the area of the reagent layer 7b is 12 mm$^2$, and the amount of maleic acid buffer carried is 0.33 nmol/mm$^2$. In this example, a reagent system 7 is composed of the CMC layer 7a and the reagent layer 7b.

An aqueous solution containing a certain amount of glucose was used as a sample solution. When the sample solution was brought into contact with the open end of the slit 10 of the sensor, the sample solution was introduced into the sample solution supply pathway by capillarity. After a lapse of a certain time (reaction time), a voltage of 500 mV was applied to the working electrode 4 with respect to the counter electrode 5, and the value of the current flowing between the working electrode 4 and the counter electrode 5 was measured. While glucose is oxidized to gluconolactone by the catalytic action of glucose oxidase, ferricyanide ions are reduced to ferrocyanide ions. The concentration of the ferrocyanide ions thus generated is proportional to the concentration of glucose in the sample solution. Therefore, based on the oxidation current thereof, glucose concentration can be measured. Gluconolactone generated at this time is decomposed by the action of gluconolactonase.

Figure 3:
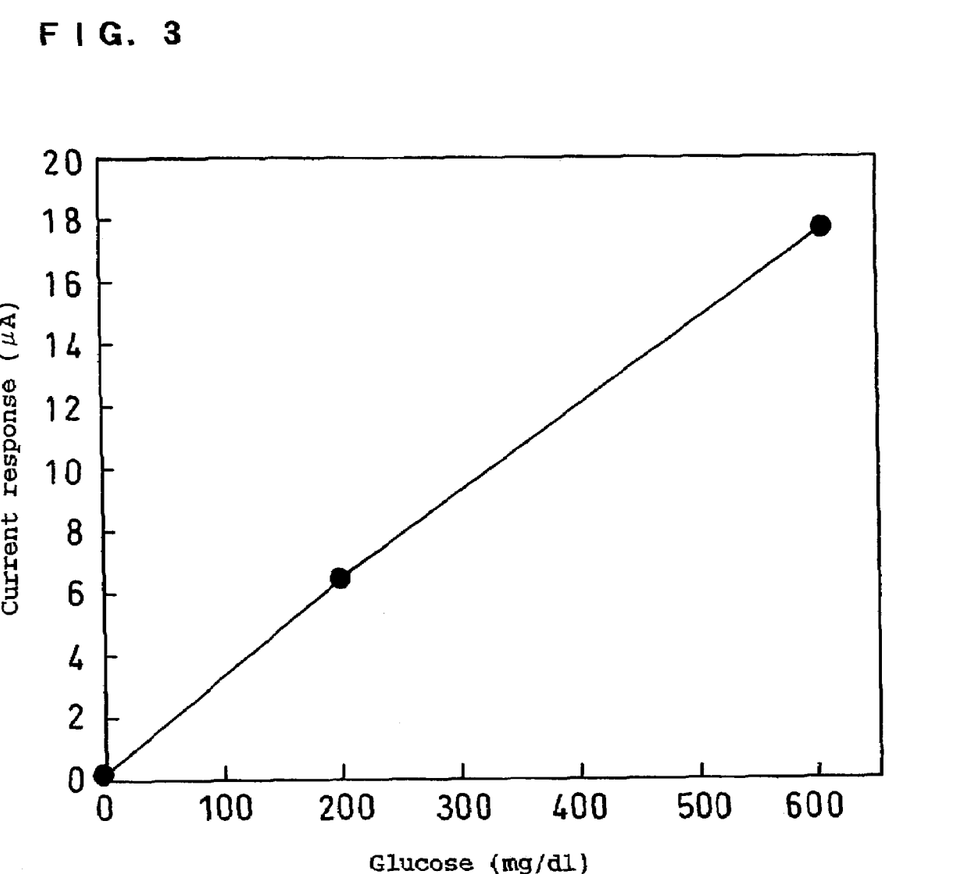
FIG. 3 is a graph indicating the response characteristics of the same biosensor.

As shown in FIG. 3, the response current obtained in a reaction time of 5 seconds was plotted against the glucose concentration in the sample solution, and as a result, a favorable linear relationship was observed between them.

From this, it has been found that the concentration of a substrate, which is a measuring target, can be quantified with good accuracy in a short reaction time of 5 seconds. This is presumably because gluconolactonase exerted sufficient activity due to the action of the buffer added into the reagent layer. Thus, presumably, gluconolactone, a product of the oxidation reaction of glucose, was promptly decomposed by gluconolactonase without being accumulated in the solution, so that the oxidation reaction of glucose was accelerated.

As described above, since sufficient response values can be obtained even in a shorter reaction time, the measuring time of the sensor can be shortened.

EXAMPLE 2

Figure 4:
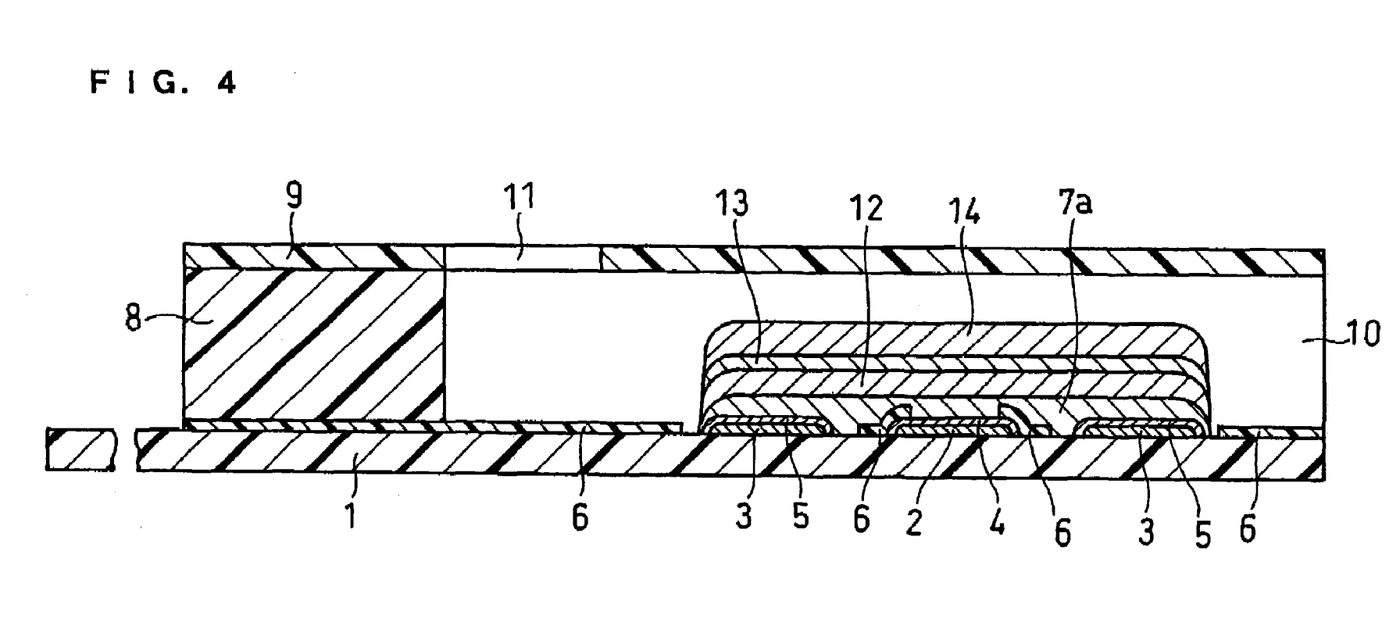
FIG. 4 is a longitudinal sectional view of the main part of a biosensor in another example of the present invention.

FIG. 4 is a longitudinal sectional view of a biosensor in this example. The difference from Example 1 is that PQQ dependent glucose dehydrogenase, which is an oxidoreductase that catalyzes the oxidation reaction of glucose, is carried by the sensor separately from gluconolactonase.

On a base plate 1 on which an electrode system was formed, a CMC layer 7a was formed by dropping a 0.5 wt % aqueous solution of CMC, which is a hydrophilic polymer, in an amount of 5 µl and drying it. Next, gluconolactonase originated from *Aspergillus niger* was dissolved in a 1 mM potassium hydrogenphthalate buffer solution (pH6), which is a buffer. 4 µl of the solution was dropped on the CMC layer 7a and was dried to form a gluconolactonase layer 12. Therein, the area of the gluconolactonase layer 12 is 12 mm$^2$, and the amount of potassium hydrogenphthalate buffer carried is 0.33 nmol/mm$^2$. Then, with the aim of separation from the gluconolactonase layer 12, a layer 13 of polyvinyl pyrrolidone (hereinafter referred to as PVP) was formed on the gluconolactonase layer 12 by dropping a 0.5 wt % aqueous solution of PVP in an amount of 5 µl and drying it. Further, PQQ dependent glucose dehydrogenase, which is an oxidoreductase that catalyzes the oxidation reaction of glucose, and potassium ferricyanide, which is an electron mediator, were dissolved in a 1 mM succinic acid buffer solution (pH5), which is a buffer. 4 µl of the solution was dropped on the PVP layer 13 and was dried to form a glucose dehydrogenase layer 14. Therein, the area of the glucose dehydrogenase layer 14 is 12 mm$^2$, and the amount of succinic acid buffer carried is 0.33 nmol/mm$^2$. The reagent system of this example is composed of the CMC layer 7a, the gluconolactonase layer 12, the PVP layer 13 and the glucose dehydrogenase layer 14.

As in this example, by spatially separating two enzymes by a soluble polymer such as PVP, a buffer adequate for each enzyme can be added to each one. In this case, since a soluble polymer such as PVP is promptly dissolved upon supply of a biological sample such as blood or a glucose aqueous solution to the biosensor, there is no fear of deteriorating the reactivity of the enzymes.

On the biosensor of this example, measurements were conducted using aqueous solutions containing certain amounts of glucose as sample solutions, and as a result, similar results to those of Example 1 were obtained.

As described above, also in the case of using two enzymes, a buffer adequate for each enzyme can be added to the vicinity of each enzyme. Thus, even when the reaction time is shorter, sufficient response values can be obtained in quantifying the concentration of the substrate to be measured, and the measuring time of the sensor can be shortened.

In the foregoing examples, the voltage applied to the electrode system was 500 mV, but there is no limitation thereto. It may be any voltage at which the electron mediator is oxidized at the working electrode. Also, as the measuring method, the method of detecting the current was used, but the subject to be detected may be any output that changes as the electrochemical reaction proceeds. For example, the quantity of electricity in a certain time may be detected. Since the quantity of electricity is an integral value of the current with respect to time, it can be correlated to the concentration of the substrate to be measured.

An insoluble carrier may be provided in the sample solution supply pathway such that one or more of the reagents contained in the above-mentioned reagent system are immobilized to the carrier. For immobilization, it is preferable to use a covalent bonding method, a cross-linking immobilization method, an adsorption method, or immobilization methods utilizing interaction of coordinate bond or specific bond.

In the foregoing examples, carbon was used as the electrode material, but there is no limitation thereto. As the working electrode material, it is possible to use any electrically conductive material which is not subject to oxidation itself upon the oxidation of the electron mediator such as carbon, platinum, gold and palladium. As the counter electrode material, it is possible to use any electrically conductive material which is used commonly such as silver and platinum in addition to carbon and gold. In addition to the working electrode and the counter electrode, an electrode having a stable potential may be used as a reference electrode. In this case, the voltage is applied between the reference electrode and the working electrode. The shape, arrangement, number, etc. of the electrode system are not to be limited to those as shown in the above examples. Also, the shape, arrangement, number, etc. of the electrode leads and terminals are not to be limited to those as shown in the above examples.

In the foregoing examples, the reagent system was described as being formed on the electrode system, but it may be formed in the vicinity of the electrode system, for example, on the top cover side, so as to be exposed to the sample solution supply pathway.

INDUSTRIAL APPLICABILITY

In the biosensor of the present invention, gluconolactone produced by the oxidation of glucose by the action of the oxidoreductase is converted to gluconic acid by gluconolactonase. This allows the oxidation reaction of glucose to proceed smoothly, and sufficient response can be obtained even when the measuring time is short. Further, since the activity of gluconolactonase or the oxidoreductase which catalyzes the oxidation reaction of glucose is improved by the buffer, the response characteristics of the sensor can be improved. As described above, the present invention can provide a biosensor that is highly responsive and capable of rapid and highly sensitive quantification of a specific component contained in a sample.

The invention claimed is:

1. A method for measuring the concentration of glucose in a sample solution by using a biosensor comprising: an electrically insulating base plate;
   an electrode system comprising a working electrode and a counter electrode disposed on said base plate; and
   a reagent system comprising an oxidoreductase which catalyzes a reaction of oxidizing glucose to gluconolactone, gluconolactonase and a buffer, wherein said buffer is selected from the group consisting of phthalic acid and its salts, maleic acid and its salts, succinic acid and its salts, phospholic acid and its salts, acetic acid and its salts, boric acid and its salts, citric acid and its salts, glycine, tris(hydroxymethyl)aminomethane, piperazine-N,N'-bis(2-ethane sulfonic acid), N-(2-acetamide)iminodiacetic acid, N,N-bis(2-hydroxyethyl)-2-aminoethane sulfonic acid, 2-morpholinoethanesulfonic acid, imidazole, dimethyl glutaric acid, triethanolamine hydrochloride, collidine, N-tris(hydroxymethyl)methylglycine, and bis(2-hydroxyethyl)iminotris(hydroxymethyl)methane, wherein said reagent system further comprises an electron mediator, and wherein the method comprises determining the concentration of glucose in a sample solution by measuring an oxidation current produced by the oxidation of an electron mediator that has been reduced as a result of oxidation of glucose.

2. The method in accordance with claim 1, wherein said reagent system further comprises a hydrophilic polymer.

3. The method in accordance with claim 1, wherein said oxidoreductase, gluconolactonase and buffer are, while being mixed, carried by the sensor.

4. The method in accordance with claim 1, wherein said oxidoreductase and gluconolactonase are, while being separated from each other, carried by the sensor.

5. The method in accordance with claim 1, wherein said gluconolactonase is originated from one selected from the group consisting of *Escherichia coli*, yeast, man, rat, swine, bovine, *Aspergillus niger*, *Azotobacter vinelandii*, *Pseudomonas fluorescens*, *Zymomonas mobilis*, *Streptomyces coelicolor*, *Deinococcus radiodurans* and *Xylella fastidiosa*.

6. The method in accordance with claim 1, wherein the amount of the buffer carried by the sensor is 5 nmol/mm$^2$ or less.

7. The method in accordance with claim 1, wherein the buffer has a buffering capacity in a range of pH 4 to 8.

8. The method in accordance with claim 1, wherein said oxidoreductase is selected from the group consisting of glucose oxidase, PQQ dependent glucose dehydrogenase, NAD dependent glucose dehydrogenase and pyranose oxidase.

9. The method in accordance with claim 1, further comprising a cover member that is disposed on the base plate to form a sample solution supply pathway to the electrode system between the cover member and the base plate.

10. The method in accordance with claim 1, wherein said reagent system further comprises an amphipathic compound.

11. A method for measuring the concentration of glucose in a sample solution by using a biosensor comprising: an electrically insulating base plate;

an electrode system comprising a working electrode and a counter electrode disposed on said base plate; and a reagent system comprising an oxidoreductase which catalyzes a reaction of oxidizing glucose to gluconolactone, gluconolactonase and a buffer, wherein said buffer is selected from the group consisting of phthalic acid and its salts, maleic acid and its salts, succinic acid and its salts, phospholic acid and its salts, acetic acid and its salts, boric acid and its salts, citric acid and its salts, glycine, tris(hydroxymethyl)aminomethane, piperazine-N,N'-bis(2-ethane sulfonic acid), N-(2-acetamide)iminodiacetic acid, N,N-bis(2-hydroxyethyl)-2-aminoethane sulfonic acid, 2-morpholinoethanesulfonic acid, imidazole, dimethyl glutaric acid, triethanolamine hydrochloride, collidine, N-tris(hydroxymethyl)methylglycine, and bis(2-hydroxyethyl)iminotris(hydroxymethyl)methane, wherein said reagent system further comprises an electron mediator, the method comprising the steps of:

supplying a sample solution including glucose to the biosensor for allowing the oxidoreductase to catalyze an oxidation of the glucose;

applying a voltage to the working electrode with respect to the counter electrode; and measuring an oxidation current produced by the oxidation of the electron mediator that has been reduced as a result of oxidation of glucose in the sample solution.

* * * * *